United States Patent [19]

Short

[11] 3,941,880
[45] Mar. 2, 1976

[54] METHOD FOR USE OF 11-LOWER ALKYL STEROIDS

[75] Inventor: George E. Short, Arlington Heights, Ill.

[73] Assignee: G. D. Searle & Co., Chicago, Ill.

[22] Filed: Sept. 16, 1974

[21] Appl. No.: 506,466

Related U.S. Application Data

[60] Division of Ser. No. 117,704, Feb. 22, 1971, Pat. No. 3,860,701, which is a continuation-in-part of Ser. Nos. 723,284, April 22, 1968, Pat. No. 3,565,991, and Ser. No. 28,934, April 15, 1970, Pat. No. 3,830,907.

[52] U.S. Cl. .................. 424/241; 424/81; 424/243
[51] Int. Cl.[2] ..................................... A61K 17/06
[58] Field of Search ........................ 424/241, 243

[56] References Cited
UNITED STATES PATENTS

| | | | |
|---|---|---|---|
| 3,499,445 | 3/1970 | Reed | 128/260 |
| 3,565,991 | 2/1971 | Short | 424/243 |
| 3,830,907 | 8/1974 | Short | 424/19 |
| 3,857,932 | 12/1974 | Shepherd et al. | 424/19 |
| 3,860,701 | 1/1975 | Short | 424/81 |

OTHER PUBLICATIONS

Fosgate, O. T. "Alteration and Control of Estrous Cycles in Bovines with analoss of Testosterone" Bull. Ga. Acad. Sci. 25:106–107 Apr. 20, 1967.

*Primary Examiner*—Shep K. Rose
*Attorney, Agent, or Firm*—John J. McDonnell

[57] ABSTRACT

The method of controlling estrus and ovulation in female bovines by the administration of 11-lower alkyl steroids and 11-lower alkyl steroid compositions for use therein.

Drug delivery system for the controlled elution of 11-lower alkyl steroids comprising the steroid adsorbed in a copolymer of a monoester of an olefinic acid and a diester of an oelfinic acid. The method of controlling estrus and ovulation in female bovines by the implantation of said drug delivery system in the bovines, followed by removal at a predetermined period, alternatively augmenting the estrus response by administration of an estrogenic compound.

5 Claims, No Drawings

METHOD FOR USE OF 11-LOWER ALKYL STEROIDS

This is a division of Ser. No. 117,704, filed Feb. 22, 1971, now U.S. Pat. No. 3,860,701, issued Jan. 14, 1975, which in turn is a continuation-in-part of applicant's prior copending applications Ser. No. 723,284, filed Apr. 22, 1968 now U.S. Pat. No. 3,565,991, issued Feb. 22, 1971 and Ser. No. 28,934, filed Apr. 15, 1970, now U.S. Pat. 3,830,907, issued Aug. 20, 1974.

This invention relates to compositions useful in treating female bovines with certain progestational steroids possessing an 11-lower alkyl substituent to attain control of estrus and ovulation and to methods of accomplishing said treatment. Such controlled estrus and ovulation is particularly useful in the course of breeding such farm animals for commercial purposes, for effecting contraception and for producing an anabolic response associated with the inhibition of estrus.

As an embodiment of this invention is also provided a novel drug delivery system comprising an 11-lower alkyl steroid, having progestational properties but being essentially devoid of estrogenic activity, adsorbed in a copolymer of a major amount of a monoester of an acrylic or methacrylic acid and a minor amount of a diester of one of said acids which diester serves as a cross-linking agent, each monomer component being chosen such that the resultant copolymer contains at least one free hydroxy group. These polymers per se and their manner of manufacture are generally described in U.S. Pat. Nos. 2,976,576 and 3,220,960, except that in the most preferred embodiment of this invention an aqueous solution is not used in the polymerization so that an anhydrous polymer is prepared instead of the hydrogels of U.S. Pat. Nos. 2,976,576 and 3,220,960. A further significant distinction lies in the fact that the steroid is added to the monomer mixture prior to polymerization in accordance with methods disclosed in the literature, suitably by the methods described in U.S. Pat. No. 2,721,871.

Progestational steroids have been administered to domestic animals orally, parenterally and intravaginally for various purposes, including the control of estrus and ovulation. One purpose of such control is to attain near simultaneous release of estrus and ovulation in large numbers of cycling animals following cessation of treatment (i.e., synchronization of estrus and ovulation), thus facilitating controlled breeding for commercial purposes, e.g., breeding by artificial insemination, natural service or hand service. Other important commercial purposes of such control are: (1) to aid in the induction of ovulation in acyclic animals, such as animals which have recently borne young so that such animals with long gestation periods have greater assurance of producing an offspring each year; (2) to aid in the induction of ovulation in animals that are near but have not reached puberty; and (3) to aid in the induction of fertile ovulation in animals with impaired fertility resulting from neurohormonal imbalances or deficiencies resulting in failure to cycle. Moreover such control can enable long term, suitably 90–180 days, contraception in female range bovines. Such control can also be employed for inhibition of estrus in feed lot heifers.

Previously, a number of progestational steroids have been used to control estrus and ovulation in selected animal species. These compounds were often used by the oral route of administration, suitably by mixing the compound with ground feed. Problems which have been encountered with such compounds and with such oral administration have involved either a too long acting effect or undesired variability in the time of release of ovulation and estrus and almost invariably impaired fertility at the first post-treatment cycle. Consequently the criteria necessary for the selection of an effective estrus and ovulation controlling agent for use in bovines have remained largely undetermined. Additionally, the practice of administering the compound mixed into the ground feed has resulted in variations attributed to differences in the feed intake from animal to animal and has also made synchronization by this means unsuitable for range cattle, which have not been or can only, with difficulty, be adapted to ground feed. To avoid the foregoing problems certain efforts have been made to incorporate a progestational steroid in an implant, illustratively consisting of sponge type material, e.g., elastic, porous and adsorptive plastics, particularly polyurethanes of the polyether or polyester type, natural sponge, natural or synthetic rubber, polyvinyl chloride or polyethylene, for use in estrus and ovulation control in animals particularly domesticated varieties. Nevertheless in certain animal species, e.g., bovines, it has been found difficult to attain estrus and ovulation control while at the same time meeting the demands of practicality and efficiency. For example, it has frequently been found that the size of implant required in order to release an effective dosage for sustained estrus and ovulation control over the treatment period is wholly impractical from the standpoint of convenience of insertion in the animal, removal from the animal, and acceptance by the animal and owner.

In accordance with this invention it has been found that selection of a suitable agent for use in estrus and ovulation control in bovines is dependent upon the compound's ability to be effective in the control of estrus and ovulation at low dosage, and to release estrus and ovulation nearly simultaneously within a short, predetermined period after discontinuance of its use while failing to appreciably interfere with and preferably enhancing fertility to the first two breedings subsequent to treatment.

Moreover it has surprisingly been discovered that a direct correlation exists between a compound's ability to exhibit such properties and its recognition as a potent progestational compound being essentially devoid of estrogenicity, i.e., a pure progestin. Potency as a progestational compound can be determined by the Clauberg assay (described in *Hormone Assay*, C. W. Emmens, Academic Press, page 422 (1950) wherein a responsive rating at least 2 on the McPhail scale is required in order for the compound to be said to exhibit progestational activity. A potency of at least 1000% as compared to progesterone, upon parenteral administration, has been found to be indicative of a potent progestational compound for the purposes of this invention. A compound can be said to be essentially devoid of estrogenicity if it evokes a response of equal to or less than 0.02% of estrone in an assay procedure adapted from that described by Allen and Doisy, *J. Am. Med. Assoc.*, 81, 819 (1923) and is described as follows:

Female rats, 60 days of age, are spayed and allowed to recover for a period of 20–30 days. At 80–90 days of age, the rats are primed with two equal injections of 2.5 mcg. (micrograms) of estrone in 0.1 ml. of corn oil spaced 24 hours apart. The vaginal mucosa is examined 56 and 72 hours after the first injection, and those animals responding positively to two courses of priming are selected for testing purposes. Each test animal is treated with 1000 mcg. of the test compound administered subcutaneously in two equal portions given 24 hours apart. Fresh smears taken from the vaginal mucosa are examined microscopically for the presence of cornified and/or round nucleated epithelial cells. Using that criterion, each smear is scored as positive or negative. A test substance is considered active if positive responses are obtained in more than 10% of the animals.

A further indication of a compound's lack of pure progestin qualities is its ability to elicit an active rating in a deciduogenic assay wherein a group of four immature female rabbits is primed by the injection of 5 mcg. of 17β-estradiol daily on each of 6 successive days. Starting on the day following the last priming injection and continuing on each of 8 successive days thereafter, a corn oil solution or suspension of 10 mgs. of the test compound is administered subcutaneously. On the 9th day the animals are sacrificed and the uteri are removed and examined histologically for evidence of decidual cell formation. Decidual cell formation is typical of that found in the uteri of pregnant rabbits and can be induced by substances such as norethynodrel. Illustrative of the 11-lower alkyl steroidal progestational compounds being essentially devoid of estrogenic activity found, according to this invention, to be suitable for control of estrus and ovulation upon oral, parenteral (e.g., subcutaneous, intramuscular or intravenous) or intravaginal administration to bovines are 17α-acetoxy-11β-methyl-19-norpregn-4-ene-3,20-dione and derivatives thereof, particularly those represented by the following general formula:

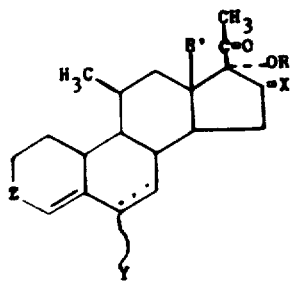

wherein R can be hydrogen or an alkanoyl radical containing 1 to 10 carbon atoms, R' a lower alkyl radical, X is H₂ or a methylene radical, Y is hydrogen or a methyl or chloro group, and Z is a carbonyl, hydroxymethylene or (lower alkanoyl)oxymethylene radical, the dotted line indicates an optional 6(7) double bond and the wavy line indicates that the substituent in the 6-position can be in the α or β stereochemical configuration. (This group of compounds is prepared according to the methods described in U.S. Pat. No. 3,527,778 and U.S. Ser. No. 45,592, filed June 11, 1970.) One particularly potent pure progestin desirably employed in the instant invention at doses as low as 0.14 mg. daily for 14–21 days upon parenteral administration is 17α-acetoxy-11β-methyl-19-norpregn-4-ene-3,20-dione.

A further group of suitable 11-lower alkyl steroidal "pure progestins" are 3-(3-oxo-11β,13β-dialkyl-17β-hydroxygon-4-en-17α-yl) propionic acid γ-lactones especially those represented by the following general structure:

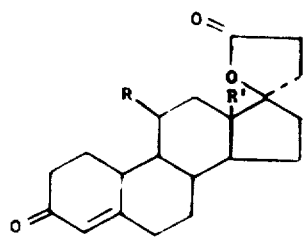

wherein R and R' are lower alkyl radicals. (These γ-lactones are prepared according to the methods described in U.S. Pat. No. 3,462,426.) A member of this group which is particularly suited for the purposes of this invention is 3-(3-oxo-11β-methyl-17β-hydroxyestr-4-en-17α-yl)propionic acid γ-lactone. This compound demonstrates effective control of estrus and ovulation of female bovines upon parenteral administration at dosages as low as 0.45 mg. daily. Similarly suitable are (optionally 17-lower alkylsubstituted) 11,13β-dialkylgon-4-en-3-ones such as those embodied in the following structural formula:

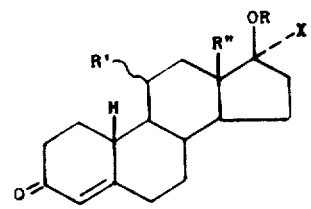

wherein R and R" are lower alkyl radicals, X is hydrogen or a lower alkyl radical, R' can be hydrogen or a lower alkanoyl radical, the wavy line indicates that the alkyl substituent at the 11-position can possess either the α or β stereochemical configuration. These compounds can be prepared according to the procedures detailed in U.S. Pat. No. 3,325,520.

The lower alkyl radical embodied in the foregoing formulas are exemplified by methyl, ethyl, propyl, butyl, pentyl, hexyl, heptyl and the branched-chain radicals isomeric therewith.

Typical of the lower alkanoyl radical signified above as well as the alkanoyl portion of the (lower alkanoyl) oxymethylene radicals appearing above are forinyl, acetyl, propionyl, butyryl, valeryl, caproyl, heptanoyl, octanoyl, nonanoyl, decanoyl, and the branched-chain isomers thereof.

In accordance with this invention the 11-lower alkyl steroidal progestational compound, being essentially devoid of estrogenic activity, is made for administration by incorporation into a pharmaceutically acceptable carrier composition convenient for the route of administration elected. Synchronization, for example, is conveniently achieved by injection of the steroidal compound in edible oils. Suitable pharmaceutical acceptable carriers for injection, i.e., to induce ovulation in acyclic animals, include water, edible oils, alcohols, glycols and oil- and water-base pastes of polyglycols.

Such compositions may additionally include agents such as isotonic and suspending agents, surfactants, preservatives, bactericidal and bacteriostatic agents.

Illustrative preparations of three concentrations of an edible oil composition containing two preferred 11-alkyl steroidal "pure progestins" are presented below.

To obtain a corn oil compositions containing 2.5 milligrams of 17α-acetoxy-11β-methyl-19-norpregn-4-ene-3,20-dione, per milliliter, 2.5 grams of the steroid were added to 950 milliliters of corn oil, with stirring, and the resulting solution was heated to about 45°C. Thereafter the solution was cooled to ambient temperature and its volume was adjusted to 1 liter with addition of oil. Stirring was continued to achieve homogeity and the solution was then filtered through a medium porosity sintered glass filter and filled into vials of the appropriate size. When 0.5 grams and 0.1 gram of the steroid were added to 950 milliliters of corn oil and the foregoing procedure was repeated, corn oil compositions containing 0.5 milligram per millimeter and 0.1 milligram per millimeter, respectively, of 17α-acetoxy-11β-methyl-19-norpregn-4-ene-3,20-dione were obtained.

To obtain corn oil compositions containing 2.5 milligrams of 3-(3-oxo-11β-methyl-17-hydroxyestr-4-en-17α-yl)propionic acid γ-lactone per milliliter, 2.5 grams of the steroid were dissolved in 100 milliliters of benzyl alcohol by stirring and heating to 40°C. After dissolution was complete, the volume was adjusted to 1 liter by the addition of corn oil. The solution was stirred until achieving homogeneity, after which time the solution was filtered through a medium porosity sintered glass filter and filled into vials of the appropriate size. When 0.5 grams and 0.1 gram of the steroid were added to 100 milliliters of benzyl alcohol and the above procedure was repeated, corn oil compositions containing 0.5 milligram per milliliter and 0.1 milligram per milliliter, respectively, of 3-(3-oxo-11β-methyl-17β-hydroxyestr-4-en-17α-yl)propionic acid γ-lactone.

Suitable pharmaceutically acceptable carriers for implantation or intravaginal insertion include non-toxic diluents and bulking agents, solid porous materials such as silicone rubber and polyurethane, in which the steroid is dispersed. The steroidal agent can also be admixed with feed, alternatively additionally combined with any of the foregoing carriers and agents.

To provide a drug delivery system for use in bovines which will achieve the goals of effective control of estrus and ovulation set forth in pages 2 and 3 while at the same time satisfying the commercial needs of convenience and practicality in intended usage, e.g., in the administration to, withdrawl from and compatibility with the bovine, in accordance with this invention, it has been found that a particularly useful carrier or support material for administering a selected 11-lower alkyl steroidal progestational compound, being essentially devoid of estrogenic activity, is a copolymer of a major amount of a monoester of a acrylic or methylacrylic acid and a minor amount of a diester of one of these acids each monomer component being chosen such that the resultant copolymer contains at least one free hydroxy group. These copolymers are generally described in U.S. Pat. Nos. 2,976,576 and 3,220,960 but are most preferably prepared without the use of water in the polymerization mixture and with the addition of the steroid to the polymerization mixture, suitably by incorporation in a monomer or the monomer mixture prior to polymerization. The monoester monomers for use in preparing the aforementioned copolymers typically include methacrylyl glycolic acid and the monomethacrylates and mono-acrylates of glycols, glycerol, di- and poly-alkylene glycols, and other polyhydroxylic compounds. The diester monomers for use in preparing the copolymer and serving as the cross-linking agents thereof include the diacrylates and dimethacrylates of glycols, glycerol, di- and poly-alkylene glycols, and other poly-hydroxylic compounds, including ethylene glycol and tri-ethylene glycol. An especially preferred and advantageous support component of the drug delivery system embodied by this invention is that copolymer prepared by combining a major amount of 2-hydroxyethyl methacrylate with a minor amount of ethylene glycol dimethacrylate. That mixture of monomers, most desirably containing the medicinal component, i.e., the pure progestin, is bulk polymerized, preferably in the presence of a known polymerization initiation (such as diisopropyl peroxydicarbonate) suitably by warming to yield the instant drug delivery system. The amount of cross-linkage in the polymerized product is directly controlled by the percentage (on a weight basis) of the cross-linking agent present in the monomer mixture. Thus in the preferred support component, described above, the amount of ethylene glycol dimethacrylate added to mixture for polymerization will be in substantially direct proportion to the amount of cross-linkage present in polymerized product. A specific illustration of the chemical preparation of an instant drug delivery system is the combining of about 4200 parts of 2-hydroxyethyl methacrylate, 43 parts of ethylene glycol dimethacrylate, 7 parts of diisopropyl dicarbonate and 750 parts of 17α-acetoxy-11β-methyl-19-norpregn-4-ene-3,20-dione and the stirring of this mixture at room temperature, or optionally with the supplying of a slight amount of heat, to effect solution. That monomer-drug mixture is than added to a series of molds, preferably of the cylindrical shape, and of the desired size, for example having an internal diameter of 5 mm. The molds are then placed in a water bath and held at temperatures up to 90°C, most preferably 75°C, for a period of approximately 25 minutes to affect polymerization. The resulting mold shaped drug delivery system now characterized by a cross-linkage substantially identical that amount of cross-linking monomer added to the preparative mixture, for example in the foregoing instance wherein ethylene glycol dimethacrylate is the cross-linking monomer, a percent cross-linkage of about 1% is achieved. Thus by varying the amount of cross-linking monomer component any desired cross-linkage can be obtained. For the purposes of this invention it has been found that cross-linkages of between 0.3 to 20% are suitable, though most preferred results are obtained in the range of 4–5% for synchronized breeding and 7–20% for prolonged inhibition of estrus. Of course, as explained below, the selection of the 11-lower alkyl "pure progestin" component is one of the determining factors in choosing a most desirable amount of cross-linkage.

It has been found, according to the discovery of this invention, that in order for the medicinal component of the drug delivery system to be effective in the control of estrus and ovulation it must not only possess the biological profile referred to above, namely it must be a progestational compound essentially devoid of estrogenic activity, but it likewise must possess the characteristic of compatibility with the support component selected, namely the polymer of which the drug delivery system is composed. As one aspect of compatibility, the medicinal component must be stable in relationship to the support component such that upon elution (e.g., in the bovine body fluids), the medicinal component will not differ in chemical constitution from the medicinal component which was adsorbed on or in the support material. As a further aspect of compatibility, the medicinal component must be sufficiently soluble in the support material and the resultant drug delivery system sufficiently soluble in the bovine body fluids such that the medicinal component will not prematurely precipitate out of the support material but will elute at a substantially constant rate from the drug delivery system to provide the systemic delivery to the bovine of an effective estrus and ovulation controlling dosage of "pure progestin" per day over the entire treatment period. Finally, the medicinal component must possess the ability to be controlled in its release rate from the drug delivery system such that constant elution is obtained over the treatment period, while simultaneously the original amount necessary for incorporation in the support material is not so large as to require the finished drug delivery system to be of a size which is impractical for use in the bovine. According to this invention, it has been discovered that each of the requirements for a medicinal component can be met by utilizing an 11-lower alkyl steroidal progestational compound, being essentially devoid of estrogenic activity, particularly one of the compounds embodied in the groups discussed hereinbefore, and most especially 17α-acetoxy-11β-methyl-19-norpregn-4-ene-3,20-dione. For the bovine it has been determined that a practical size of drug delivery system is within the range of about 3–10 millimeters in diameter, by about 15–65 millimiters in length. The drug delivery system herein provided by this invention may be administered by any practical method consistent with animal acceptance and can be suitably achieved by subcutaneous implantation in various receptive animals sites, e.g., between the center and the base of the ear, in the neck, jaw or area of the tail head of the bovine; minor modifications of device design would permit intravaginal administration. The well known susceptibility of the ear to excessively low ambient temperatures with a resulting predisposition to constriction of the blood vessels located in it may dictate a preference for an alternative implantation site under certain conditions.

The dosage of the medicinal component contained in the drug delivery system is obviously dependent upon the choice of particular support material and 11-lower alkyl steroidal progestational compound, being essentially devoid of estrogenic activity. The route of administration, the cyclical status of the animal to be treated and specific nature of the desired results are additional factors that would influence the dose and treatment regimen.

Generally, considering all of the various purposes to be achieved by the control of estrus and ovulation, the most preferred drug delivery system of this invention is that in which the medicinal component is 17β-acetoxy-11β-methyl-19-norpregn-4-ene-3,20-dione and the support component is that polymer prepared generally in accord with the procedure described above from the monomers 2-hydroxyethyl methacrylate and ethylene glycol dimethacrylate and having a cross-linkage percentage of 0.3–20%.

Where the 11-lower alkyl steroidal "pure progestin" is to be administered over a period of two or more days by means of one or more drug delivery system each delivery system should contain 1.5–4 fold, or greater multiples of the total dosage to be administered to insure than an adequate amount of compound enters the system of the cow over the entire treatment period. Thus, the preferred drug delivery system for use in the control of estrus and ovulation to effect synchronized breeding in cycling animals should desirably contain at least about 3 milligrams and preferably 6 milligrams of an 11-lower alkyl steroidal progestational compound being essentially devoid of estrogenic activity, e.g., 17α-acetoxy-11β-methyl-19-norpregn-4-ene-3,20-dione. For control of estrus and ovulation in the female bovine to effect inhibition of estrus or contraception for 90–180 days each drug delivery system should contain preferably 30–60 milligrams of an 11-lower alkyl steroidal progestational compound being essentially devoid of estrogenic activity, e.g., 17α-acetoxy-11β-methyl-19-norpregn-4-ene-3,20-dione. Of course, the amount of medicinal component can vary with any difference in potency in the 11-lower alkyl steroidal "pure progestin" selected and the use to which it is to be put.

A convenient shape and size of drug delivery system for use in the bovine can consist of any compatible shape, particularly a cylindrical shape for example in the form of a rod or tube, having a diameter of 0.3 to 1.0 cm. and a length of 1.5 to 6.5 cm. Particularly preferred dimensions for synchronized breeding use are a diameter of 0.3 cm. and a length of 1.8 cm. when the medicinal component is 17α-acetoxy-11β-methyl-19-norpregn-4-ene-3,20-dione. The cylindrical shape and this particular size has been advantageously selected for use in bovines, particularly by the subcutaneous route of administration, because the shape affords both maximum surface area into which the chosen concentration of 11-alkyl steroidal "pure progestin" can be adsorbed or disbursed and ease of instrumentation in implantation thus avoiding disruptive psychological problems and rejection or lack of acceptance on the part of the animal. Since it has been established that there is a linear relationship between rate of elution and surface area of the drug delivery system available for contact with tissue fluids, as well as rate of elution and concentration of the steroid to be released, it was desired to select a drug delivery system which would permit the maximum coordination of these factors. Additionally, the relatively small size is preferable from the standpoint of facilitating implantation under the skin (e.g., minor incisions are required) and avoiding untoward psychological reactions on the part of the implantor. Consequently, since the surface area available for contact with tissue fluid was substantially predetermined in the bovine along with a suitable site for implantation this factor had to be maximized by an appropriate selection of steroid which would provide a concentration at which control could be achieved and would hopefully provide an advantageous rate of elution from the support material. When it was determined that the 11-lower alkyl "pure progestin," of this invention were characterized by a unique property of their rate of elution from the preferred support material being responsive to the amount of cross-linking agent incorporated in the polymer, it was appreciated that such a factor combined with the high potency, stability and solubility of the selected compound made its usage surprisingly and advantageously compatible with the preferred support material to provide an unusually effective drug delivery system.

Because of the maximizing of each of the significant factors affecting the rate of the elution of the steroid into the animal, it has been found that this technique of administration to a bovine, preferably by implantation of an instant drug delivery system permits a desirable lowering of the effective dose required to accomplish synchronization, reduces the number of times an animal need be handled, effects a maximum practical control over the dose as a factor of time and its removal provides for a precise and sharp termination of treatment not obtainable with other methods of administration, particularly per oral. Desirably, the drug delivery system should contain sufficient 11-lower alkyl steroidal "pure progestin" to permit the release of at least the dosage required to control estrus and ovulation upon constant infusion per day. In the instance of the most preferred embodiment of this invention, namely the instant drug delivery system containing 17α-acetoxy-11β-methyl-19-norpregn-4-ene-3,20-dione as the medicinal component should permit the release of at least 0.14 milligram per day. To achieve this effect it has been determined, as indicated above that the 11-lower alkyl steroidal "pure progestin" drug delivery system should contain 1.5–4 fold multiples of the total dosage to be administered to insure that an adequate amount of the compound enters the system of the cow over the entire treatment period.

This drug delivery system can be provided with a means for easy withdrawl at any desired time. Specifically, in order to remove the drug delivery system at will, it can be provided with cord-like means affixed to the composition by incorporating the cord-like means into the mold prior to polymerization or by incorporating the composition in a mesh-like enclosure having cord-like withdrawal means at one or each end of the enclosure. A mesh-like enclosure, as opposed to a solid enclosure not having an open texture, can be desirable for the drug delivery system since such an enclosure permits the surface of the implant composition to contact the tissue fluids, thus enabling elution. Upon implantation, these cord-like withdrawal means will protrude from the skin openings. If necessary to secure the drug delivery system in place, the two ends may be tied together. To accomplish easy removal, tension is applied to a free protruding withdrawal means. Because of ready availability and relative inexpensiveness, silver-plated copper mesh has been chosen as a sufficient and desirable material from which to make the mesh-like enclosure; other materials suitable for forming mesh-like enclosures can be employed such as woven cloth, plastics such as polyvinyl or polyethylene, or the like. Silver-plated copper mesh has been found sufficient in that it can be twisted and formed to enclose the implant composition and provide the withdrawl means. Also, it minimizes the number of crypts in which microorganisms can take refuge from body defenses, it has great tensile strength and it evokes little or no tissue reaction.

It has been advantageously found that the above described drug delivery system also can be used in the following manner for synchronization of breeding. At the time of implantation a single injection of at least 5 milligrams of estradiol valerate or an equivalent biological amount of another similarly long-acting estrogen which serves to promote regression of the corpora lutea, is simultaneously administered. The drug delivery system is then retained in the animal for a period of nine or ten days. These animals would then be bred in respect to manifestation of estrus. Optionally, animals which have been treated for 14–16 days with the instant 11-alkyl steroidal progestin drug delivery system alone or for 9–10 days in accordance with the immediately preceding procedure can be intramuscularly administered 0.5 to 2 milligrams of 17β-estradiol or an equivalent biological amount of another physiologically compatible estrogen such as diethyl stilbestrol, 24 hours after drug delivery system removal. These animals can then be artificially inseminated 30–48 hours after estrogen administration without reference to manifestations of estrus. In lieu of the administration of 17β-estradiol or its equivalent, an intra-muscular injection of 400–1500 IU (International Units) pregnant mare serum gonadotropin or other suitable gonadotropin may be administered at the time of drug delivery system removal and the animals artificially inseminated within 3 days thereafter without regard to manifestations of estrus.

The following examples are given by way of illustrating the invention and are not to be construed as limiting. Unless otherwise indicated, amounts of material given in parts are parts by weight.

EXAMPLE 1

Seventeen cycling beef heifers were administered, by subcutaneous implantation, an instant drug delivery system containing 6 milligrams of 17α-acetoxy-11β-methyl-19-norpregn-4-ene-3,20-dione adsorbed in the polymerized product of the combination of 2-hydroxyethyl methacrylate and ethylene glycol dimethacrylate which was characterized by a 4% content of the cross-linking monomer. The drug delivery systems were removed after 21 days and all 17 heifers came into estrus within 48 hours.

EXAMPLE 2

Thirty-seven cycling beef heifers were given a drug delivery system of the instant invention by subcutaneous implantation without regard to the stage of their estrus cycles. Each drug delivery system contained 6 milligrams of 17α-acetoxy-11β-methyl-19-norpregn-4-ene-3,20-dione adsorbed in a support material prepared from 2-hydroxyethylmethacrylate and ethylene glycol dimethacrylate according to the polymerization procedure discussed above and characterized by a 4.8% content of cross-linking monomer. Thirty-five of the 37 heifers came into estrus within 72 hours after drug delivery system removal on the 21st day post implantation.

EXAMPLE 3

One hundred and twenty beef heifers were randomly assigned to three groups of 40 each. Heifers in group one were administered, by subcutaneous implantation in the ear, a drug delivery system of this invention containing 6 milligram of 17α-acetoxy-11β-methyl-19-norpregn-4-ene-3,20-dione adsorbed in the polymer prepared from 2-hydroxyethyl methacrylate and ethylene glycol dimethacrylate according to the procedure discussed above and characterized by a cross-linkage content of about 4.8%. The drug delivery systems were removed on the 17th day and it was observed that 90% of the heifers came into estrus within 38 hours.

Heifers in group two were given drug delivery systems identical with those given to group one by the same technique, namely subcutaneous implantation in the ear. At the same time, each heifer was given an injection of 5 milligrams of estradiol valerate. Upon removal of the drug delivery systems on the 10th day post treatment, 98% of the heifers came into estrus within 110 hours.

Heifers in control group three were each given, by subcutaneous implantation, a drug delivery system identical to that described for group one except that the medicinal component was omitted. The delivery system was removed on the 10th day post implantation and 10% of the heifers were observed to come into estrus within 96 hours after removal.

Thirty-seven, 39 and 38 of the heifers in groups one, two, and three, respectively, were artificially inseminated as detected in estrus. Pregnancy diagnosis made 41 and 55 days after treatment was terminated disclosed that 11/37 (30%) in group one, 24/39 (62%) in group two and 27/38 (71%) in group three conceived to first service and 27/37 (68%), 32/39 (80%) and 28/38 (70%) conceived to service at all times detected in estrus during a 26-day period starting on the day the drug delivery systems were removed from all heifers in each of the three groups.

What is claimed is:

1. A method of controlling ovulation and estrus in female bovines which comprises the subcutaneous administration of an 11-lower alkyl steroidal progestational compound selected from the group comprising 17α-acetoxy-11β-methyl-19-norpregn-4-ene-3,20-dione and 3-(3-oxo-11β-methyl-17β hydroxyestr-4-en-17α-yl) propionic acid γ lactone, being essentially devoid of estrogenic activity, to said female bovines.

2. The method according to claim 1 in which the compound is 17α-acetoxy-11β-methyl-19-norpregn-4-ene-3,20-dione.

3. The method according to claim 1 in which the compound is 3-(3-oxo-11β-methyl-17β-hydroxyestr-4-en-17α-yl)propionic acid γ-lactone.

4. The method according to claim 2, in which the amount of said 11-lower alkyl steroidal progestational compound administered is at least 0.14 milligram per day.

5. The method according to claim 1 in which the compound is administered over a 14–21 day period.

* * * * *